(12) United States Patent
Wakayama et al.

(10) Patent No.: US 6,641,526 B1
(45) Date of Patent: Nov. 4, 2003

(54) DEVELOPMENT OF NORMAL OFFSPRING FROM OOCYTES INJECTED WITH FREEZE-DRIED SPERMATOZOA

(75) Inventors: Teruhiko Wakayama, Honolulu, HI (US); Ryuzo Yanagimachi, Honolulu, HI (US)

(73) Assignee: University of Hawaii, Honolulu, HI (US)

(*) Notice: Subject to any disclaimer, the term of this patent is extended or adjusted under 35 U.S.C. 154(b) by 0 days.

(21) Appl. No.: 09/177,391

(22) Filed: Oct. 23, 1998

Related U.S. Application Data
(60) Provisional application No. 60/078,925, filed on Mar. 20, 1998, and provisional application No. 60/089,938, filed on Jun. 19, 1998.

(51) Int. Cl.$^7$ ............. A61B 17/43; A61D 7/00; A61K 35/52; A61K 35/54; A01N 1/02
(52) U.S. Cl. ............. 600/33; 424/561; 435/2; 435/348; 435/349; 435/350; 435/351; 435/352; 435/353; 435/354; 435/363; 435/366; 435/374
(58) Field of Search ............. 424/561; 435/2, 435/348, 349, 350, 351, 352, 353, 354, 363, 366, 374; 600/33

(56) References Cited

U.S. PATENT DOCUMENTS 5,849,473 A   12/1998   Cabrera et al. ............. 435/2

OTHER PUBLICATIONS

Ohsumi et al. J. Exper. Zool., 237:319–325, 1986.*
Watanabe et al., J. Fac. Fish. Anim. Husb., 11:33–37, 1972.*
Hughes, Cryobiology, 10:342–344, 1973.*
Asahina et al., Cryobiology, 15:122–127, 1978.*
Chao et al., Proceedings of the National Science Council, Republic of China, Part B, Life Sciences, 10:145–149, 1986.*
Behlmer et al., Int. J. Invertebrate Reproduction and Development, 7:193–199, 1984.*
Bedford, J.M. & Cooper, H.I. The occurrence and possible functional significance of –S–S– crosslinks in sperm heads with particular reference to eutherian mammals. *J. Exp. Zool.* 188, 137–156 (1974).
Bialy, G. & Smith, V.R. Freeze–drying of bovine spermatozoa. *J. Dairy Sci.* 40, 739–745 (1957).
Bunge, R.G., Keettel, W.C. & Sherman, J.K. Clinical use of frozen semen. *Fertil. Steril.* 5, 520–529 (1954).
Catt, J. & O'Neill, C. Manipulation of sperm before intracytoplasmic sperm injection improves fertilization. *Fertil. Steril.* 64, 1210–1212 (1995).
Chatot, C.L., et al. An improved culture medium supports development of random–bred 1–cell mouse embryos in vitro. *J. Reprod. Fert.* 86, 679–688 (1989).

Chatot, C.L., et al. Development of 1–cell embryos from different strains of mice in CZB medium. *Biol. Reprod.* 42, 432–440 (1990).
Day, J.G. & McLellan, M.R. (eds.). *Cryopreservation and freeze–drying protocols.* (Methods in Molecular Biology, vol. 38) Humana Press, Totawa, NJ (1995). Virus Cryopreservation and Storage, pp. 7–20; Freeze–Drying and Cryopreservation of Bacteria, pp. 21–30; Freeze–Drying of Yeasts, pp. 31–38; Cryopreservation and Freeze–Drying of Fungi, pp. 49–62; Cryopreservation of the Sperm of the Pacific Oyster, pp. 145–150; Cryopreservation of Fish Spermatozoa, pp. 151–166; Cryopreservation of Avian Spermatozoa, pp. 167–178; Cryopreservation of Semen from Domestic Livestock, pp. 189–198; Cryopreservation of Human Gametes, pp. 221–234.
Dozortsev, D., et al. Sperm plasma membrane damage prior to intracytoplasmic sperm injection: a necessary condition for sperm nucleus decondensation. *Human Reprod.* 10, 1960–1964 (1995).
Goto, K., et al. Fertilization of bovine oocytes by the injection of immobilized, killed spermatozoa. *Vet. Rec.* 127, 517–520 (1990).
Jeyendran, R.S., Hunter, A.S. & Graham, E.F. Alteration of seminal proteins during freezing of bovine semen. *J. Dairy Sci.* 66, 887–891 (1983).
Katayose, H., Matsuda, J. & Yanagimachi, R. The ability of dehydrated hamster and human sperm nuclei to develop into pronuclei. *Biol. Reprod.* 47, 277–284 (1992).
Kimura, Y. & Yanagimachi, R. Intracytoplasmic sperm injection in the mouse. *Biol. Reprod.* 52, 709–720 (1995).
Kimura, Y., et al. Analysis of mouse egg activation suggests the involvement of sperm perinuclear material. *Biol. Reprod.* in press (1998).
Kimura, Y., and Yanagimachi, R. Mouse oocytes injected with testicular spermatozoa or round spermatids can develop into normal offspring. *Development* 121, 2397–2405 (1995).
Kuretake, S., et al. Fertilization and development of mouse oocytes injected with isolated sperm heads. *Biol. Reprod.* 55, 789–795 (1996).

(List continued on next page.)

*Primary Examiner*—Peter Paras
(74) *Attorney, Agent, or Firm*—Jones Day (57) ABSTRACT

The invention provides a method for freeze-drying spermatozoa to obtain at least one reconstituted spermatozoon whose head (nucleus) is capable of fertilizing an oocyte to produce a live offspring. The motility of spermatozoa which have been freeze-dried and stored in a vacuum at room temperature is not restored when rehydrated. Their plasma membranes are disrupted and they are all "dead" in the conventional sense. However, when they are injected microsurgically into oocytes, their nuclei transform into male pronuclei and participate in normal embryonic development.

29 Claims, 3 Drawing Sheets

(1 of 3 Drawing Sheet(s) Filed in Color)

OTHER PUBLICATIONS

Larson, E.V. & Graham, E.F. Freeze–drying of spermatozoa. in *International Symposium on Freezing Biological Products* (eds. Cabasso, V.J. & R.H. Regamey) 36, 343–348 (S. Karger, Basel, 1977).

Meryman, H.T. Drying of living mammalian cells. *Ann. New York Acad. Sci.* 85, 729–739 (1960).

Nakagata, N. Use of cryopreservation techniques of embryos and spermatozoa for production of transgenic (Tg) mice and for maintenance of Tg mouse lines. *Lab. Anim. Sci.* 46, 236–238 (1996).

Nei, T. & Nagase, H. Attempts to freeze–dry bull spermatozoa. *Low Temp. Sci. Bull.* 19, 107–116 (1961).

Palermo, G., et al. Pregnancies after intracytoplasmic injection of a single spermatozoon into an oocyte. *Lancet* 340, (Jul. 4), 17–18 (1992).

Polge, C., Smith, A.U. & Parkes, A.S. Revival of spermatozoa after vitrification and dehydration at low temperature. *Nature* 164, 666–676(1949).

Polge, C. & Rowson, L.E.A. Fertilizing capacity of bull spermatozoa after freezing at –79°C. *Nature* 169, 626–627 (1952).

Saacke, R.G. & Almquist, J.O. Freeze–drying of bovine spermatozoa. *Nature* 192, 995–996 (1961).

Schatten, G. The centrosome and its mode of inheritance: the reduction of the centrosome during gametogenesis and its restoration during fertilization. *Dev. Biol.* 165, 299–335 (1994).

Schultz, R.M. & Kopf, G.S. Molecular basis of mammalian egg activation. in *Current Topics in Developmental Biology* 30, 21–62 (eds. Petersen, R.A. & G. Schatten), (1995).

Sherman, J.K. Freezing and freeze–drying of human spermatozoa. *Fert. Steril.* 5, 357–371 (1954).

Sherman, J.K. Cryopreservation of human semen. in *CRC Handbook of the Laboratory Diagnosis and Treatment of Infertility* (eds. Keel, B.A. & B.W. Webster), 229–269 (CRC Press, Boca Raton, Florida, 1990).

Singh, S.G. & Roy, D.J. Freeze–drying of bovine semen. *Indian J. Vet. Sci.* 37, 1–7 (1967).

Smith, A.U. & Polge, C. Survival of spermatozoa at low temperatures. *Nature* 166, 668–669(1950).

Swann, K. The soluble sperm oscillogen hypothesis. *Zygote* 1, 273–279 (1993).

Uehara,T. & Yanagimachi, R. Microsurgical injection of spermatozoa into hamster eggs with subsequent transformation of sperm nuclei into male pronuclei. *Biol. Reprod.* 15, 467–470 (1976).

Wakayama, T., Whittingham, D.G. & Yanagimachi, R. Production of normal offspring from mouse oocytes injected with spermatozoa cryopreserved with or without cryoprotection. *J. Reprod. Fert.* 112, in press (1998).

Watson, P.F. Artificial insemination and the preservation of semen, in *Marshall's Physiology of Reproduction*, 4th Ed. (ed. G.E. Lamming) vol. 2, 748–869 (Churchill Livingston, London, 1990).

Yanagida, K., et al. Thermostability of sperm nuclei assessed by microinjection into hamster oocytes. *Biol. Reprod.* 44, 440–447 (1991).

Yanagimachi, R. The mammalian oocyte's response to intracytoplasmic sperm injection. in *Microscopy of Reproduction and Development: A Dynamic Approach*. (ed. P.M. Motta), in press (Antonio Delfino Editore, Rome, 1997).

Yuschenko, N.P. Proof of the possibility of preserving mammalian spermatozoa in a dried state. *Proc. Lenin Acad. Agr. Sci.* 22, 37–40 (1957) (cited from jeyendran, R.S. et al. supra).

Downs, S.M. & Mastropolo, A.M. The participation of energy substrates in the control of meiotic maturation in murine oocytes. *Develop. Biol.* 162, 154–168 (1994).

Yanagimachi, Y. Mammalian Fertilization. Chapter 5, pp. 189–317, in The Physiology of Reproduction, Second Edition, Eds. E. Knobil and J.D. Neill, Raven Press, Ltd., New York (1994).

* cited by examiner

DEVELOPMENT OF NORMAL OFFSPRING FROM OOCYTES INJECTED WITH FREEZE-DRIED SPERMATOZOA

This application claims the benefit of U.S. Provisional Patent Applications, Ser. No. 60/078,925, filed Mar. 20, 1998, and Ser. No. 60/89,938, filed Jun. 19, 1998.

The U.S. Government has a paid-up license in this invention and the right in limited circumstances to require the patent owner to license others on reasonable terms as provided for by the terms of contract No. R01-HD-03402 awarded by the National Institutes of Health, Public Health Service.

BACKGROUND OF THE INVENTION

The invention relates to the freeze-drying of spermatozoa, the fertilization of oocytes with reconstituted freeze-dried spermatozoa, and the development of live offspring therefrom.

The successful cryopreservation of sperm by the use of cryoprotectants and the ability to store the frozen sperm for long periods of time has produced dramatic improvements in animal husbandry as well as human reproductive medicine. It has been found that cryoprotected frozen-thawed spermatozoa often regain their motility and fertilize almost as efficiently as fresh spermatozoa.

Long term storage of spermatozoa in liquid nitrogen (−196° C.) has been routinely used to cryopreserve cattle and human spermatozoa. However, conventional sperm preservation is very expensive in the long term because of the need for a constant supply of liquid nitrogen. Moreover, in certain areas of the world it may be inconvenient and/or expensive to store spermatozoa in liquid nitrogen, such as in developing countries where liquid nitrogen (or even dry ice) may not be readily accessible. Transporting of conventionally frozen spermatozoa is also problematic in that it may require the transport of large liquid nitrogen tanks or the use of special shipping containers containing liquid nitrogen or dry ice. Thus, many attempts have been made to preserve spermatozoa without requiring storage in liquid nitrogen. For example, if fertilization-competent spermatozoa could be stored in a freeze-dried state at ambient temperatures or in ordinary refrigerators, the reduction in the maintenance and shipping costs could be enormous.

It is believed that the first recorded attempt to freeze-dry spermatozoa was in 1949, when one milliliter (ml) of fowl semen was mixed with an equal volume of Ringer's solution containing 20–30% glycerol, spread as a thin layer in a distillation flask, and "freeze-dried" by removing 90% of the water. When the preparations were rehydrated within 2 hours after being brought back to room temperature, it was reported that up to 50% of spermatozoa regained motility. The fertility of the rehydrated spermatozoa, however, was never determined.

Subsequent attempts to produce live offspring using freeze-dried spermatozoa have not been successful. It has been reported, for example, that a live calf was born following artificial insemination of a cow with bull spermatozoa that were reconstituted immediately after freeze-drying and showed 50% sperm motility. It was also reported that twelve litters of normal rabbits were obtained by insemination using freeze-dried spermatozoa. However, neither of these results could be repeated by the originators or duplicated and confirmed by others working in the field.

From studies of the properties and fertility of normal and frozen-thawed spermatozoa, it is known that spermatozoa are not required to be "alive" in the conventional sense (i.e., having intact plasma membranes) in order for them to support normal embryonic development. For example, in an intracytoplasmic sperm injection (ICSI) technique, motile human spermatozoa are selected. They are immobilized ("killed") immediately before injection into an oocyte by aggressive abrasion of their tails resulting in damage to the plasma membrane. It has been reported that sperm immobilization significantly increases the rate of successful fertilization by ICSI. It has also been reported that when mouse spermatozoa were suspended in media without any cryoprotectant, then immediately frozen in liquid nitrogen, 100% of the spermatozoa were "dead" as judged by live/dead cell staining, and yet normal embryonic development occurred after microinjection of the heads of the thawed spermatozoa into oocytes. There has also been a report of the birth of two normal calves after microinjection into oocytes of spermatozoa killed by freeze-thawing without any cryoprotectants.

Although it is known that freeze-dried hamster and human sperm heads injected into hamster oocytes can form normal looking pronuclei, it has never been determined whether such sperm heads can support normal embryonic development. Moreover, it has been demonstrated that loss of motility, acrosome damage and enzyme release occur when spermatozoa are frozen and dried to a moisture content of less than 30%, 7% and 0.5%, respectively. Evidence has also been obtained that cellular proteins in spermatozoa are altered by dehydration below 6% moisture.

In view of the foregoing, there is a need for a reliable and reproducible method for freeze-drying spermatozoa, by which the freeze-dried sperm retain their fertilization competency during long periods of storage at ambient, or ordinary refrigerator temperatures or below. There is a further need for a method for sperm injection that employs rehydrated freeze-dried sperm to fertilize recipient oocytes, resulting in normal live offspring.

SUMMARY OF THE INVENTION

The invention provides a method for freeze-drying spermatozoa to obtain at least one reconstituted spermatozoon whose head (nucleus) is capable of fertilizing an oocyte to produce a live offspring. The method of the invention comprises the steps of: (a) collecting live spermatozoa; (b) suspending the spermatozoa in a suspension medium; (c) freezing the suspension of spermatozoa; and (d) drying the suspension of spermatozoa to a moisture level that is less than 1%, preferably less than 0.01%, more preferably less than 0.001%, and especially less than 0.00001%. The method may further comprise the step of rehydrating the freeze-dried suspension of spermatozoa, wherein at least one rehydrated spermatozoon head retains its genetic integrity and is capable of fertilizing an oocyte to produce a live offspring. As discussed below, the method may further comprise the step of storing the freeze-dried spermatozoa prior to rehydrating.

To obtain a live offspring, at least the head (nucleus) of a rehydrated spermatozoon is inserted into an isolated oocyte to form a fertilized oocyte. The sperm head is inserted into the oocyte by microinjection, preferably by piezo electrically-actuated microinjection. Preferably, the insertion of the nucleus takes place within one hour of rehydration. The fertilized oocyte is then allowed to develop into an embryo and implanted into the uterus of a foster mother where it develops into a live offspring.

In some species (e.g., most eutherian mammals, including humans), normal embryonic development of the fertilized oocyte also requires the insertion of the paternal centrosome associated with the sperm nucleus. The centrosome is normally attached either to the posterior end of the sperm head or to the anterior end of the sperm tail when the head and tail are separated. Thus, in embodiments of the invention, a sperm-associated centrosome from another spermatozoon may be inserted simultaneously with the sperm head, or may be inserted by means of simultaneous or consecutive insertion of the sperm tail. Alternatively, insertion of the sperm nucleus and centrosome may be accomplished by insertion of an entire rehydrated spermatozoon into the oocyte.

It has been discovered that spermatozoa that are freeze-dried by the method of the invention may be stored for at least three months or, more preferably, for at least a year, at temperatures ranging from ambient (e.g., room temperature) to refrigerator temperatures (e.g., about 4° C.) without losing their genetic integrity or fertilization capability. Thus, the freeze-dried spermatozoa prepared by the method of the invention, can retain their competency during shipping to virtually anywhere in the world at ambient or refrigerator temperatures, and may also undergo short term storage at ambient or refrigerator temperatures in locations where liquid nitrogen or dry ice are not readily available. Preferably, long term (e.g., indefinite) storage of the freeze-dried sperm takes place at temperatures of less than 4° C. (e.g., -20° C. or below).

The method of the invention may be used to freeze-dry spermatozoa of both invertebrate and vertebrate species including, but not limited to, invertebrates such as the sea urchin, lobster, abalone, shellfish, and the like, and vertebrates such as fish, amphibians, reptiles, birds, and all mammals.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DETAILED DESCRIPTION OF THE INVENTION

During normal fertilization in mammals, a fertilizing spermatozoon ascends the female genital tract, passes through the oocyte's vestments, then fuses with an oocyte. Sperm fusion with the oocyte triggers activation of the oocyte. The activated oocyte resumes meiosis and oocyte chromosomes transform into a female pronucleus. Meanwhile, the sperm nucleus within the oocyte decondenses to transform into a male pronucleus. Fully developed female and male pronuclei then unite and chromosomes from these pronuclei mingle. The resultant zygote develops into a live offspring.

The present invention provides a method for freeze-drying spermatozoa that, upon rehydration, are capable of fertilizing isolated oocytes to produce live offspring. The freeze-dried spermatozoa produced by the method of the invention retain their genetic and reproductive potential even though, when rehydrated, they are motionless and "dead" in the conventional sense. When the whole sperm or isolated sperm heads (i.e., containing all head components including the nucleus) or the demembranated sperm or sperm heads (i.e., retaining the nucleus and perinuclear materials, but lacking plasma membranes) of the spermatozoa of the invention are injected directly into oocytes, normal fertilization and embryonic development occurs, which can result in the production of live offspring. Preferably, the sperm head (nucleus) is inserted directly into the cytoplasm of the oocyte. The insertion of the sperm head is by microinjection, preferably by piezo electrically-actuated microinjection. As discussed further below, embryonic development of the fertilized oocytes of some species may require the simultaneous or sequential injection of a sperm centrosome. If the centrosome does not survive the freeze-drying process, a centrosome may be harvested from an unfrozen spermatozoon for insertion into the oocyte.

The individual steps and substeps of the methods of the invention for the preparation of fertilization competent freeze-dried sperm and their use in an in vitro fertilization procedure are now presented in greater detail.

Preparation of Spermatozoa

In order to ensure that as many as possible of the freeze-dried sperm retain their genetic integrity throughout the freeze-drying process of the invention, it is preferred that physiologically mature spermatozoa be used in the method of the invention. In mature spermatozoa, DNA is associated with basic proteins called protamines. In mammals, protamines are extensively cross-linked by disulfide bonds. This stabilizes the sperm nuclei and renders them very resistant to physical and chemical disruption. Cross-linking of nuclear protamines occurs mainly during transit of the spermatozoa through the epididymis. Thus, mammalian spermatozoa within the epididymis and in ejaculate (semen) are generally physiologically more mature than those within the testis, and are preferred in the methods of the invention, at least in mammals.

Mature spermatozoa from invertebrates and vertebrates are collected by methods known to those skilled in the art. For example, mature spermatozoa of rodents, such as mouse, golden (Syrian) hamster, guinea pig, rabbit, and the like, may be collected from *caudae epididymes*; whereas, in other species, such as humans, pigs, horses, bulls, goats, fowl, and the like, mature spermatozoa may be isolated from freshly ejaculated semen of fertile males. Spermatozoa of fish (e.g., swordtail, *Xiphophorus helleri*) and invertebrates, such as sea urchins (*Tripneustes gratilla*), may be collected from the testes of mature males.

An example of a method for obtaining spermatozoa from a cauda epididymis follows. A cauda epididymis is removed from a mature male mouse (approximately 8 weeks after birth or older). The blood and adipose tissue are removed from the surface of the cauda epididymis. It is then compressed to release a dense mass of spermatozoa. A drop (about 2 µL) of sperm mass is placed in the bottom of 1.5 ml polypropylene centrifuge tubes and overlaid with 0.5 ml of warm physiological medium (e.g., CZB medium, phosphate buffered saline, or isotonic saline). After about 10 to 20 minutes at 37° C., motile spermatozoa may be collected from the supernatant.

An example of a method for obtaining spermatozoa from semen follows. Freshly ejaculated human semen is allowed to liquefy for about 30 minutes at room temperature (about 25° C.). The semen is then diluted with about 10 ml of saline and filtered through about two layers of tissue paper to remove debris. The filtrate may then be centrifuged at 400×g for about 10 minutes, and the sedimented spermatozoa resuspended in a physiological solution at a desired concentration for the freeze-drying process.

An example of a method for obtaining spermatozoa from testes follows. An excised testes is placed in an erythrocyte-lysing buffer (e.g., 155 mM $NH_4Cl$, 10 mM $KHCO_3$, 2 mM EDTA, pH 7.2–7.4), minced using a pair of fine scissors, and filtered through about two layers of tissue paper to remove debris. The filtrate is then centrifuged (e.g., 700×5 minutes) and the pellet is resuspended in a physiological solution at a desired concentration in preparation for the freeze-drying process.

Regardless of the method used for preparation of the spermatozoa, more than 50% of the recovered spermatozoa should be motile.

The spermatozoa so recovered are suspended in a physiological medium, described below, in preparation for the freeze-drying process. Alternatively, the spermatozoa may undergo further processing to obtain demembranated sperm heads prior to freeze-drying.

Preparation of Demembranated Sperm Heads

Demembranated sperm heads are detergent-extracted heads that lack all membranes, including the plasma membrane and inner and outer acrosomal membranes, but retain the nucleus and perinuclear material. For example, sperm heads may be demembranated by treatment with Triton X-100 with or without SDS (sodium dodecyl sulfate). Triton X-100 is a well known non-ionic surfactant that is widely used for removal of membrane components under non-denaturing conditions. SDS is an anionic detergent used to solubilize various proteins, including membrane proteins. In the mouse, sperm heads demembranated by using Triton X-100 have been shown to be capable of activating oocytes, leading to normal embryonic development.

An exemplary method for demembranating sperm heads follows. An aliquot of a sperm suspension, prepared as above, is sonicated. For example, spermatozoa collected from caudae epididymes, testes, or semen, as above, may be suspended in 5 ml BM buffer (75 mM NaCl, 24 mM EDTA, and 50 mM Tris-HCl, pH 7.2) and sonicated for 30 seconds at 70%–80% output of a Biosonik sonicator (Bronwill Scientific, Rochester, N.Y.). Over 95% of spermatozoa are decapitated by this treatment. To demembranated the sperm heads, the sonicated sperm suspension is centrifuged at 700×g for 5 minutes, and the pellet is washed with BM buffer and then treated at room temperature for 5 minutes with 1% Triton X-100 in NIM medium. (NIM medium consists of 123.0 mM KCl, 2.6 mM NaCl, 7.8 mM $NaH_2PO_4$, 1.4 mM $KH_2PO_4$, 3 mM $Na_2EDTA$, having a pH of 7.2). The heads are then rinsed thoroughly with NIM medium and resuspended in sperm suspension medium in preparation for the freeze-drying process.

Spermatozoa Suspension Media

In preparation for freeze-drying, spermatozoa (or demembranated sperm heads) are suspended in a physiological solution that is sufficient to support the integrity of at least the nucleus of the spermatozoa under normal conditions. The solution should be a balanced salt solution with at least a suitable osmotic pressure and pH. There is no single medium which can support the survival of spermatozoa of all animal species. For example, a suitable solution for sea urchin spermatozoa is seawater, with about 1,000 milli-osmols of osmotic pressure and a pH value of about 8.2. Seawater, however, will kill mammalian spermatozoa instantly. Mammalian spermatozoa require a solution having an osmotic pressure of about 300 milli-osmols and a pH of 7.0–7.6. Such a solution, however, would kill sea urchin spermatozoa.

In view of the foregoing, the suspension medium for spermatozoa must be selected according to the species of interest, according to criteria that are well known to those skilled in the art. Such selection may be made without undue experimentation. Because the spermatozoa do not have to be membrane-intact (they can be "dead") in order to successfully fertilize oocytes by injection, there is no absolute requirement for a cryopreservative, such as glycerol or the like, in the suspension medium.

Packaging

The sperm suspension may be placed into a variety of differing containers including, but not limited to glass ampules or plastic cryotubes (cryovials) which are screw-capped, or the suspension may be drawn into plastic straws which, following the freeze-dry process, may be sealed by a powder sealant, by heat, or with nylon plugs. The volume of sperm suspension in each package is not critical. Typically, a volume of about 50–100 µL is used in a 2 ml ampule.

Freeze-drying of Sperm

The suspension of spermatozoa may be frozen slowly or quickly, by known means. For example, the suspension may be frozen in liquid nitrogen vapor or in the refrigerated air of a mechanical (electrical) freezer by methods which are well known in the art. Cooling and freezing may be accomplished with a manual static or stepwise regime, or in an electronically automated and programmed liquid nitrogen-fed system. Various rates of freezing (e.g., 1° C.–25° C./minute) may be employed. For example, the freezing step may be carried out at –196° C. for 10 minutes.

Various modifications can be used in successful vapor freezing of the suspension in straws, ampules or cryotubes. A metal container (canister) with cigar tubes, or other holders with straws, or holders or racks with ampules or cryotubes, can be placed directly into liquid nitrogen vapor by using a liquid nitrogen refrigerator.

Drying of the frozen sperm suspension under vacuum, may be accomplished by a variety of different systems known to those skilled in the art. For example, a known apparatus is a VirTis model 10-020 (VirTis Co., Gardiner, N.Y.). The suspension is dried to a moisture level that is less than 1%. However, it is preferable that the moisture level be less than 0.01%, more preferably less than 0.001%, and especially less than 0.00001%. The container with freeze-dried spermatozoa is preferably vacuum-sealed, or sealed in the presence of an inert gas, such as nitrogen or argon.

Storage

The containers of freeze-dried spermatozoa are preferably stored in the dark, or wrapped with aluminum foil, or the like. For long term storage, it may be preferably to store the containers at temperatures of –20° C. or less. It is expected that, like comparably freeze-dried bacteria, fungi, and the like, the freeze-dried sperm nuclei will retain their genetic integrity indefinitely under these storage conditions. However, the containers can be stored at ambient temperature (e.g., room temperature) or ordinary refrigerator temperature (about 4° C.) for periods of time in excess of three months without compromising the ability of the freeze-dried sperm nuclei to fertilize oocytes. Therefore, the freeze-dried sperm can be shipped without the necessity for special conditions or bulky containers.

Rehydration of Freeze-dried Sperm

The freeze-dried sperm preparation is preferably rehydrated by adding pure water, the volume of which is the same as the original volume of the sperm suspension before freeze-drying. Once rehydrated, any physiological salt solution, such as 0.9% saline or CZB medium (see below), can be used for dilution. The dilution volume is not critical. The concentration of spermatozoa in the final rehydration medium should be sufficient to facilitate the retrieval of individual sperm or individual sperm heads for purposes of sperm injection into oocytes, as described below.

The incidence of oocyte activation and normal fertilization following sperm head injection appears to decrease with increasing time after sperm rehydration. The allowable time period between rehydration and injection may vary between species; however, as an example, this time period for mouse spermatozoa is preferably one hour or less.

Microscopic Examination of Rehydrated, Freeze-dried Spermatozoa

Freeze-dried, rehydrated spermatozoa are non-motile. Viability of the spermatozoa may be assessed by using any staining method that is capable of distinguishing between spermatozoa that are, in the conventional sense, live or dead. A suitable commercially available viability test kit for use in the invention is Live/dead FertiLight, available from Molecular Probes, Eugene, Oregon, which differentiates between plasma membrane-intact (live) and plasma membrane-damaged (dead) cells according to a fluorescence pattern under a UV microscope after staining with propidium iodide/SYBR 14. The nuclei of "live" spermatozoa with intact plasma membranes fluoresce green, whereas those of "dead" spermatozoa fluoresce bright orange-red. It is expected that all of the examined spermatozoa will be "dead" in the conventional sense.

Figure 2:
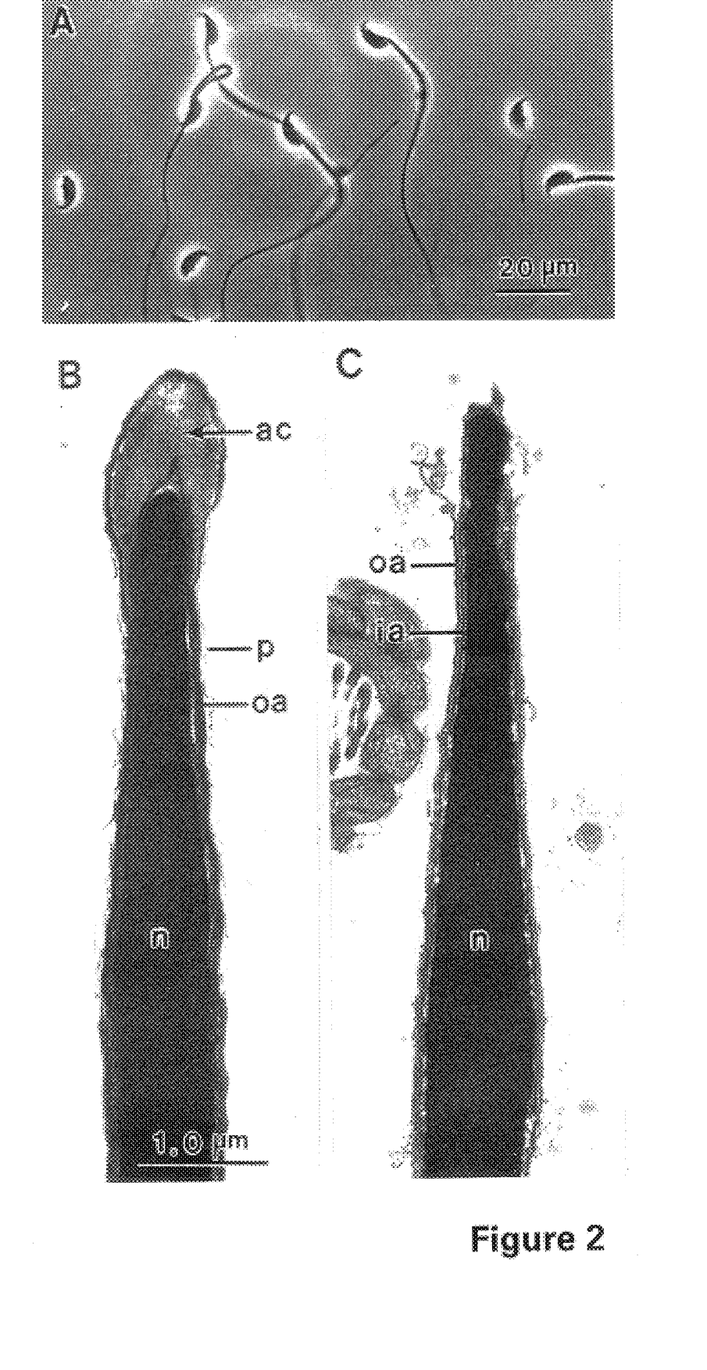
FIG. 2A is a photomicrograph of freeze-dried mouse spermatozoa immediately after rehydration. The proportion of sperm heads without tails or with broken tails varies depending on how gently or roughly dried specimens are handled during storage.
FIG. 2B is an electron micrograph showing a longitudinal cross-section through the anterior region of a normal sperm head that has not been frozen.
FIG. 2C is an electron micrograph showing longitudinal and horizontal cross-sectional views through the anterior region of a freeze-dried sperm head after rehydration. The plasma membrane (p) and contents of the acrosome (ac) are missing. (ia)=inner acrosomal membrane, (oa)=outer acrosomal membrane, (n)=nucleus.
Figure 3:
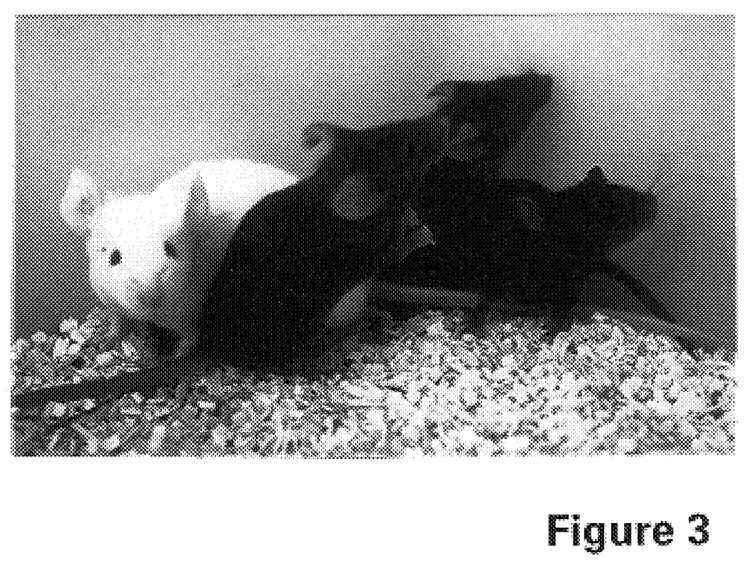
FIG. 3 is a photograph of three young (black) mice born to a CD-1 (albino) foster mother. These young developed from B6D2F1 oocytes injected with B6D2F1 spermatozoa which had been kept at room temperature for one month after freeze-drying.

FIG. 2A is a photomicrograph of representative freeze-dried mouse spermatozoa immediately after rehydration. The heads and tails of some spermatozoa are separated. The proportion of spermatozoa with broken or missing tails may vary depending on how gently or roughly dried specimens are handled during storage. Spermatozoa with or without tails are used in the injection procedure described below.

The differences between a fresh (not freeze-dried), live spermatozoon and the spermatozoon freeze-dried and rehydrated by the method of the invention are illustrated in: FIGS. 2B and 2C, respectively. Each of these Figures represents a longitudinal cross-section through the anterior region of the sperm head. Although the freeze-dried, rehydrated sperm has retained the nucleus (n), a portion of the outer acrosomal membrane (oa) and a portion of the inner acrosomal membrane (ia), both the plasma membrane (p) and the contents of the acrosome (ac) are missing.

The Recipient Oocytes

Recipient oocytes may be obtained, for example, by inducing an animal to ovulate or super-ovulate by injections of gonadotrophic hormones (for example, sequential administration of equine and human chorionic gonadotrophins) and surgical harvesting of oviductal ova shortly after the expected time of ovulation (e.g., 13–15 hours after injection of human chorionic gonadotrophin in the mouse).

Alternatively, ovarian oocytes are collected and cultured in a medium to allow their maturation, as is known to those skilled in the art. An example of preferred culture medium is modified Eagle's medium (MEM) supplemented with bovine serum albumin (BSA), as described in Downs, S. M. and A. M. Mastropolo, *Develop. Biol.* 162: 154–168, 1994 for mouse oocytes.

Sperm Components Necessary for Successful in Vitro Fertilization

It is known that, in the mouse, normal fertilization can be achieved by injecting isolated sperm heads into oocytes, and that the plasma and acrosomal membranes and all tail components are not essential for normal embryo development. The mouse and, perhaps, most common laboratory rodents are "exceptional" in that a sperm centrosome is not required for normal fertilization and, during normal fertilization, the sperm centrosome in the neck region of the spermatozoon is destined to degenerate within the oocyte after fertilization.

In contrast, in most other eutherian mammals, including cattle and humans, the sperm centrosome plays a central role in the formation of the microtubules which are essential for the union of male and female pronuclei, as well as in the subsequent cleavages during embryonic development. Therefore, in these species, the introduction of both a sperm nucleus (head) and a centrosome into an oocyte seems to be essential for the production of normal offspring. It is not known at this time whether the sperm centrosome from all species can survive freeze-drying. If not, a centrosome from an unfrozen sperm must be injected into an oocyte together with the freeze-dried sperm head in order to secure normal embryonic development. Introduction of excessive numbers of centrosomes, however, would result in abnormal pronuclear development and abnormal embryonic development.

The centrosome is normally attached either to the posterior end of the sperm head or to the anterior end of the sperm tail when the head and tail are separated. Thus, the sperm centrosome may be inserted into the oocyte simultaneously with the sperm head, or may be inserted by means of simultaneous or consecutive insertion of the sperm tail. Alternatively, insertion of the sperm nucleus and centrosome may be accomplished by insertion of an entire rehydrated spermatozoon into the oocyte.

Insertion of Spermatozoa Nucleus into Recipient Oocyte

The entire spermatozoon can be injected into the cytoplasm of the recipient oocyte, but in species in which the spermatozoa are large, an isolated sperm head (nucleus) is preferably injected directly into the cytoplasm of a recipient oocyte by a microinjection technique. In a preferred method of microinjection of a rehydrated sperm head or rehydrated demembranated sperm heads into a recipient oocyte, the piezo electrically-driven micropipette is used.

A suitable piezo electric driving unit is sold under the name of Piezo Micromanipulator/Piezo Impact Drive Unit by Prime Tech Ltd. (Tsukuba, Ibaraki-ken, Japan). The unit utilizes the piezo electric effect to advance, in a highly controlled, rapid manner, the (injection) pipette holder a very short distance (approximately 0.5 $\mu$m). The intensity and duration of each pulse can be varied and are regulated by a control unit.

For injection into an oocyte, a single spermatozoon is aspirated, tail first, into an injection pipette having a short, flat tip with an inner diameter of about 5 $\mu$m housed in the piezo electrically-actuated unit according to the instructions of the vendor. The sperm head and tail are separated by applying a single or a few Piezo pulses to the neck region. The head is then drawn deeply into the pipette.

Throughout the injection of the sperm head (nucleus), the oocyte is anchored by a conventional holding pipette. The tip of the injection pipette containing a selected sperm head is brought into intimate contact with the zona pellucida of an oocyte and several piezo pulses (using controller setting scales of intensity 1–5, speed 4–6) are applied to advance the pipette while maintaining a light negative pressure within. When the tip of the pipette has passed through the zona pellucida, the resultant zona plug is expelled into the perivitelline space and the sperm head is pushed forward until it is near the tip of the pipette. The pipette tip is then apposed to the plasma membrane and advanced (toward the opposite face of the oocyte) and the holding pipette almost reaches the opposite side of the cortex of the oocyte. The oocyte plasma membrane is now deeply invaginated around the tip of the injection needle. Upon application of one to two piezo pulses (intensity 1–2, speed 1), the oolemma is punctured at the pipette tip, as indicated by a rapid relaxation of the oolemma, which may be clearly visible. The sperm head is then expelled into the ooplasm with a minimum amount (about 6 $\mu$L) of accompanying medium. The pipette is then gently withdrawn, leaving the newly introduced head within the cytoplasm of the oocyte. This method is performed briskly, typically in batches of 10–15 oocytes which at all other times are maintained in culture conditions.

Alternative microinjection variants, in which a conventional injection pipette is employed, may be used to inject sperm heads. An example of a suitable microinjection method employing a conventional pipette, for injecting a sperm head into hamster oocyte, is described in Yanagida, K., Yanagimachi, R., Perreault, S. D. and R. G. Kleinfeld, *Biology of Reproduction* 44, 440–447 (1991), the disclosure of which pertaining to such method is hereby incorporated by reference.

Microinjection of the sperm head/demembranated sperm head offers several advantages. First, sperm head delivery by microinjection is applicable to a wide variety of spermatozoa types, irrespective of size, morphology, and the like. Second, microinjection allows carefully controlled co-injection (with the donor sperm head) of additional agents into the oocyte at the time of sperm head injection. These are exemplified below. Third, in the embodiment of the invention wherein insertion of the sperm head is by piezo electrically-actuated microinjection, rapid and efficient processing of samples is afforded, thereby reducing trauma to sperm and oocytes undergoing manipulation. The oocytes of some species (e.g., mouse) are not amenable to microinjection using conventional needles, whereas piezo electrically-actuated microinjection affords a high success rate.

Activation of Fertilized Oocytes

It is known that the mouse oocyte can be activated by injection of a single, intact mouse spermatozoon or its isolated head. Isolated sperm tails are unable to activate the oocyte. Active sperm-borne oocyte-activating factor(s) typically appear during transformation of the round spermatid into the spermatozoon. The action of these factors is not highly species-specific because mouse oocytes are activated by injection of spermatozoa from foreign species, such as the hamster, rabbit, pig, human and even fish. It has been reported that one such activating factor is a 33 kilodalton protein residing in the equatorial segment region of the acrosome. This protein, called oscillin, is readily extractable from mature (hamster) spermatozoa by simple freezing and thawing. Besides oscillin, mature spermatozoa appear to carry another activating factor that is not readily extractable, but may be obtained by sequential treatment of spermatozoa with Triton X-100 and SDS. It is not known whether the readily extractable oscillin and the freeze/thaw extraction-resistant factors are biologically and chemically identical.

It is known that sperm heads sonicated in the presence of Triton X-100 lose all components but the nucleus and perinuclear materials. Yet, when microsurgically injected into oocytes, such Triton X-100-treated sperm heads (having the nucleus and perinuclear materials, but no plasma membranes) can activate oocytes as efficiently as intact spermatozoa.

As described in the Examples below, at least in the mouse, sperm-borne oocyte-activating molecules must be resistant to freeze-drying because the majority of the oocytes that survived the injection of freeze-dried sperm heads were activated and fertilized normally.

If in other species the injection of the sperm head does not serve to activate the oocyte, activation may take place by parthenogenic means, such as by electroactivation, injection of one or more oocyte-activating substances, or transfer of the oocytes into media containing one or more oocyte-activating substances. Reagents capable of providing an activating stimulus (or combination of activating stimuli) include, but are not limited to, sperm cytoplasmic activating factor, and certain pharmacological compounds (e.g., $Ca^{2+}$ and other signal transduction modulators), which may be introduced by microinjection after, or concomitantly with, injection of the sperm head. Some activating stimuli are provided following transfer of the fertilized oocytes to media containing one or members of a sub-set of activating compounds, including stimulators of $Ca^{2+}$ release (e.g., caffeine, $Ca^{2+}$ ionophores such as A 23187 and ionomycin, and ethanol), modulators of phosphoprotein signaling (e.g., 2-aminopurine, staurospurine, and sphingosine), inhibitors of protein synthesis (e.g., A 23187, cycloheximide), 6-dimethylaminopurine, or combinations of the foregoing (e.g., 6-dimethylaminopurine and ionomycin). In one embodiment of the invention, activation of mouse oocytes is achieved by culture for 1–6 hours in $Ca^{2+}$-free CZB medium containing 2–10 mM $Sr^{2+}$.

Development of Embryos to Produce Viable Fetuses and Offspring

Following pronucleus formation, the embryo may be cultured in vitro until it reaches the 2–8 cell stage or morula/blastocyst stage, at which time the embryo may be transferred into the oviduct or uterus of a foster mother.

Simultaneous Injection of Biologically Interesting Substances With Sperm Heads

In one embodiment of the invention, microinjection of the sperm head into an oocyte permits the introduction, prior to, during, or after the injection of the sperm head into the oocyte, of one or more agents with the potential to alter the developmental outcome of the embryo. For example, ribonucleic acid (RNA) or deoxyribonucleic acid (DNA) may be introduced into the oocyte by microinjection prior to or following injection of the sperm head. For example, injection of recombinant DNA harboring the necessary cis-active signals may result in the transcription of sequences present on the recombinant DNA by resident or co-injected transcription factors, and subsequent expression of encoded proteins with an antagonistic effect on development inhibitory factors, or with a positive effect on embryo development. Moreover, the transcript may possess antisense activity against mRNAs encoding development inhibitory proteins. Alternatively, antisense regulation may be achieved by injecting nucleic acids (or their derivatives) that are able to exert an inhibitory effect by interacting directly with their nucleic acid target(s) without prior transcription within the oocyte.

Recombinant DNA (linear or otherwise) introduced by the method of the invention may comprise a functional replicon containing one or more expressed, functional gene under the control of a promoter exhibiting anything from a narrow to a broad developmental expression profile. For example, the promoter might direct immediate, but brief expression where that promoter is active only in the early zygote. Introduced DNA may either be lost at some point during embryonic development, or integrate at one or more genomic loci, to be stably replicated throughout the life of the resulting transgenic individual. In one embodiment, DNA constructs encoding putative "anti-aging" proteins, such as telomerase or superoxide dismutase, may be introduced into the oocyte by microinjection. Alternatively, such proteins may be injected directly.

EXAMPLES

The following examples illustrate the method of the invention and the development of live offspring from oocytes injected with reconstituted freeze-dried spermatozoa. In particular, the examples illustrate the development of normal mice from mouse oocytes injected with the heads (nuclei) of reconstituted freeze-dried mouse spermatozoa that had been stored either at room temperature (about 25° C.) or in a refrigerator (about 4° C.). The sperm-suspension medium prior to freeze-drying was either CZB or DMEM, described below.

The examples described herein are intended to be only examples of oocytes and spermatozoa from an animal species, sperm-suspending media, freezing protocols, storage conditions, rehydration media, and the like, that may be used in the process of the invention, and are not intended to be limiting, as other examples of embodiments of the invention would readily be recognized by those skilled in the art.

Media and Reagents

All inorganic and organic compounds were purchased from Sigma Chemical Co. (St. Louis, MO) unless otherwise stated.

Harvested oocytes were kept in CZB medium (Chatot, et al., 1989. *J Reprod. Fert.* 86, 679–688), prior to sperm injection. CZB medium comprises 81.6 mM NaCl, 4.8 mM KCl, 1.7 mM $CaCl_2$, 1.2 mM $MgSO_4$, 1.8 mM $KH_2PO_4$, 25.1 mM $NaHCO_3$, 0.1 mM $Na_2EDTA$, 31 mM Na.lactate, 0.3 mM Na.pyruvate, 7 U/ml penicillin G, 5 U/ml streptomycin sulfate, and 4 mg/ml bovine serum albumin. The medium for oocyte collection from oviducts, subsequent treatments and micromanipulation was a modified CZB containing 20 mM Hepes, a reduced amount of $NaHCO_3$ (5 mM) and bovine serum albumin (BSA) at 3 mg/ml. This medium is herein termed Hepes-CZB. For microinjection purposes, it was preferred to replace the BSA in the Hepes CZB with 0.1 mg/ml polyvinyl alcohol (PVA, cold water soluble, average molecular mass 10×103) because PVA kept the wall of the injection pipette less sticky over a longer period of time than BSA and was beneficial during repeated use of a single pipette for multiple sperm head/oocyte transfers.

Two different sperm suspending media were employed to suspend spermatozoa prior to freeze drying: (1) CZB medium without ethylenediaminetetraacetic acid (EDTA) containing 4 mg/ml BSA; and (2) Dulbecco's modified Eagle's medium (DMEM) supplemented with 10% (v/v) fetal bovine serum (Hyclone, Logan, Utah).

Preliminary experiments were performed to investigate what was the "best" sperm suspending medium for this purpose and were conducted by first suspending fresh spermatozoa in CZB medium, followed by centrifuging and resuspending in one of the media listed below, and then immediately freeze-drying the sperm. The tested sperm suspending media included (a) distilled water, (b) 34% sucrose in distilled water, (c) 180 mg/ml raffinose plus 5 mg/ml BSA, (d) 0.90% NaCl with 5 mg/ml BSA, (e) 0.9% NaCl with 1 mg/ml glucose plus 5 mg/ml BSA, and (f) lactate-free and calcium-free CZB. Only the latter medium (f) was shown to be as good as the regular CZB in its ability to keep sperm nuclei development-competent during freeze-drying (data not shown).

Animals

Animals used in these examples were maintained in accordance with the guidelines of the Laboratory Animal Service at the University of Hawaii and those prepared by the Committee on Care and Use of Laboratory Animals of the Institute of Laboratory Resources National Research Council (DHEW publication no. [NIH] 80–23, revised in 1985). The protocol of animal handling and treatment was reviewed and approved by the Animal Care and Use Committee at the University of Hawaii.

Example 1

Spermatozoa Preparation

Four different preparations of freeze-dried spermatozoa were made in order to illustrate the effects of sperm suspending medium, storage temperature and storage time period, on the ability of freeze-dried sperm nuclei to participate in the development of live offspring after injection into oocytes, as described below and illustrated in Table 1. For each preparation, two caudae epididymides of a mature B6D2F1 male mouse were used. While applying finger pressure to each epididymis, its distal portion was punctured with sharp forceps. A dense sperm mass oozing out of the epididymis was transferred into a 1.5 ml polypropylene tube containing 1 ml of one of two the test media, CZB or DMEM, described above. After incubation for 30 minutes at 37.5° C., the upper 0.3–0.5 ml of the medium was removed from the tube. Over 90% of the spermatozoa in this suspension (approximately $3–10×10^6$ per ml) were actively motile.

Example 2

Freeze-drying of Spermatozoa

An aliquot (100 μL) of the sperm suspension was put in a 2 ml ampule (Wheaton Scientific, Millville, N.J., catalogue No. 651506) which was plunged directly into liquid nitrogen. Ten minutes later, ampules were placed in a pre-cooled (−50° C.) freeze-flask attached to a freeze-dry system (Model 10-020, VirTis Co., Gardner, N.Y.). The inlet pressure was approximately 1 milliTorr. About 12 hours later, the flask was removed from the system after it had been filled with argon supplied by way of a gas-drying jar (Fisher Scientific, Pittsburgh, Pa. catalogue No. 09-204). Each ampule was connected to a vacuum pump and frame-sealed after more than greater than 99% of the gas was pumped out of it. Ampules were individually wrapped with aluminum foil and stored in the dark at room temperature (about 25° C.) or at 4° C.

Figure 1:
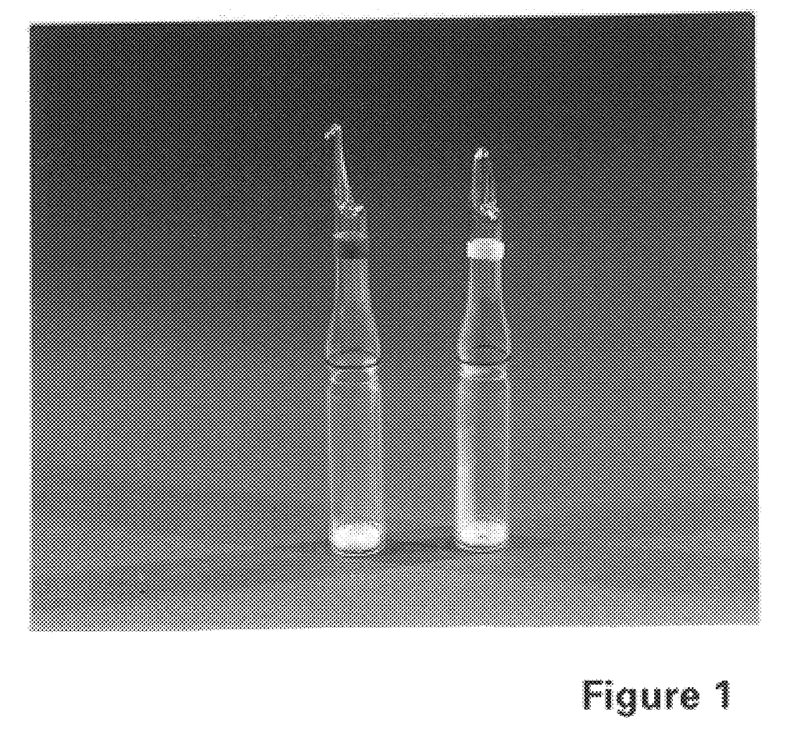
FIG. 1 is a photograph of vacuum-sealed ampules containing freeze-dried mouse spermatozoa. The white powder at the bottom of each ampule is dried CZB medium containing spermatozoa.

Ampules of freeze-dried mouse spermatozoa, prepared as above, are illustrated in FIG. 1. The white powder at the bottom of each ampule is dried CZB medium containing spermatozoa.

Example 3

Rehydration of Freeze-dried Sperm

An ampule containing freeze-dried sperm prepared as above was broken and 100 μL of distilled water were added to the ampule to form a reconstituted sperm suspension. Then 5 μL of the sperm suspension was thoroughly mixed with 50 μL Hepes-CZB containing 12% (w/v) polyvinylpyrrolidone (average molecular weight 360,000). The rehydrated sperm were observed microscopically and only those with intact heads and tails were selected for further manipulation.

Example 4

Shipping of Freeze-dried Spermatozoa

An experiment was performed to ascertain whether freeze-dried spermatozoa, prepared according to the method of the present invention, could be shipped abroad and still retain their competency to fertilize oocytes upon rehydration. In this experiment, a few ampules of freeze-dried epididymal spermatozoa were hand-carried during a three week trip to Japan that originated in Honolulu, Hi. Before freeze-drying, the spermatozoa were suspended in CZB medium. No special precautions were taken for preserving the spermatozoa, except that the ampules were wrapped with aluminum foil and kept in a cardboard box during the entire trip. Ambient temperature varied between 5° C. and 30° C. One week after their return to Honolulu, the spermatozoa were rehydrated and employed in the method of the invention.

Example 5

Oocyte Preparation

Mature B6D2F1 (C57BL/6XDBA/2) females were induced to superovulate by injecting each mouse with 7.5 International Units (IU) pregnant mare serum gonadotropin followed by 7.5 IU human chorionic gonadotropin (hCG) 48 hours later. Fourteen hours after hCG injection, cumulus-oocyte complexes were collected from oviducts and treated with bovine testicular hyaluronidase (300 USP U/ml; ICN Biochemicals, Costa Mesa, Calif.) in Hepes-CZB medium for 3 minutes to disperse cumulus cells. Prior to injection with sperm nuclei, the oocytes were rinsed and stored in CZB medium for up to 4 hours at 37° C. in an atmosphere of 5% $CO_2$ in air.

Example 6

Microinjection of Sperm Nuclei into Oocytes

For injection of sperm heads into the prepared oocytes, a microinjection chamber was prepared by employing the cover (10 mm in depth) of a plastic dish (100 mm×15 mm; Falcon Plastics, Oxnard, Calif., catalogue no. 1001). A row consisting of two round droplets and one elongated droplet was placed along the center line of the dish. The first droplet (2 µL; 2 mm in diameter) was for pipette washing (Hepes-CZB containing 12% [w/v] PVP, average molecular weight 360,000 daltons). The second droplet (2 µL; 2 mm in diameter) was the suspension of rehydrated freeze-dried spermatozoa in CZB or DMEM, prepared as above. The third elongated droplet (6 µL; 2 mm wide and 6 mm long) was Hepes-CZB medium for the oocytes. Each of these droplets was covered with mineral oil (Squibb and sons). The dish was placed on the stage of an inverted microscope interference contrast optics.

Microinjection of sperm nuclei into oocytes was achieved by the piezo-electric microinjector method described previously, employing the Piezo Micromanipulator Model MB-U by Prime Tech Ltd. (Tsukuba, Ibaraki-ken, Japan). This unit uses the piezo electric effect to advance the pipette holder a very short distance (e.g., 0.5 µm) at a time at a very high speed. The intensity and speed of the pulse were regulated by the controller.

For injection into an oocyte prepared as above, a single spermatozoon was aspirated, tail first, into an injection pipette (about 5 µM I.D. at the tip) which had been attached to the Piezo electric pipette driving unit. The sperm head and tail were separated by applying a single or a few Piezo pulses to the neck region. The intensity and speed (frequency) of the pulses were regulated by the controller PMAS-CT01 (controller setting scales: intensity 2, speed 1). The heads were then drawn deeply into the pipette and a small volume (about 0.5 µL) of mercury was placed in the proximal end of the injection pipette.

Meanwhile, a mature unfertilized oocyte was positioned on a microscope stage in Hepes-CZB medium. The oocyte was held by a holding pipette and the tip of the injection pipette was brought into intimate contact with the zona pellucida at the 3 o'clock position. Several piezo-pulses (intensity 1–2, speed 1–2) were given to advance the pipette while a light negative pressure was applied to it. When the tip of the pipette had passed through the zona pellucida, a cylindrical piece of the zona pellucida in the pipette was expelled into the perivitelline space. After the head of the spermatozoon was pushed forward until it was near the tip of the injection pipette, the pipette was advanced mechanically until its tip almost reached the opposite side of the oocyte's cortex. The oolemma was punctured by applying 1 or 2 Piezo pulses (intensity 1–2, speed 1) and the head of the spermatozoon was expelled into the ooplasm with a minimum amount (about 6 pL) of accompanying sperm suspension medium. After as much as possible of the medium was retrieved, the pipette was gently withdrawn, leaving the head of the spermatozoon within the ooplasm. All injections were performed in Hepes-CZB at room temperature (23°–27° C.) within 1 hour of sperm rehydration. Each oocyte was injected with one sperm head. Approximately 5–20 oocytes were microinjected by this method within 10–15 minutes.

Example 7

Oocyte Examination and Embryo Transfer

Sperm head-injected oocytes were incubated in CZB at 37° C. under 5% $CO_2$ in air and examined with an inverted microscope 5–6 hours later. Those with two distinct pronuclei and a second polar body were considered normally fertilized and cultured for 4 days in CZB. Those reaching the morula or blastocyst stages were transferred into the uterine horns of recipient CD-1 females (albino) which had been mated with vasectomized CD-1 males three days previously to synchronize embryonic developmental stages with that of the uterine endometrium. A mean number of eight morulae/blastocysts were transferred into each horn. Females were allowed to deliver and raise their surrogate offspring (with black, brown or grey coats). Some mature male and female offspring were randomly selected and mated to examine their fertility.

RESULTS

Microscopic Examination of Rehydrated, Freeze-dried Spermatozoa

Microscopic observation of the rehydrated spermatozoa showed that 100% of the sperm were non-motile. Sperm viability was assessed by using a commercially available cell viability test kit (Live/dead FertiLight, Molecular Probes, Eugene, Oreg.) which differentiates between plasma membrane-intact (live) and plasma membrane-damaged (dead) cells according to a fluorescence staining pattern under a UV microscope. The nuclei of "live" spermatozoa with intact plasma membranes fluoresced green, whereas those of "dead" spermatozoa fluoresced bright orange-red. Over 10,000 spermatozoa from four males were examined after freeze-drying and rehydration. All of the examined spermatozoa were "dead", as evaluated by this test.

Development of Mouse Oocytes Injected with Heads of Freeze-dried Spermatozoa As illustrated in Table 1, 1,236 of 1,353 oocytes (91.4%) survived the injection microsurgery and, of the survivors, 1,157 (93.6%) were activated by the sperm nuclei and fertilized normally, regardless of the original sperm-suspension medium (CZB or DMEM), storage temperature (25° C. or 4°), and storage time period (1 day, 2 weeks, 1 month or 3 months).

The maximum storage period of ampules in these Examples, was 3 months at 4° C. In three experiments, 57 oocytes from three females were injected with 3 month-stored spermatozoa. 95% of the injected oocytes survived the microsurgery, and all of them were fertilized normally. 91% of fertilized eggs developed to morulae/blastocysts in vitro. Fourteen (30%) of 46 embryos transferred to three foster mothers developed into normal adults.

The majority (90%–93%) of fertilized eggs, that had been injected with CZB-suspended sperm heads, that had been freeze-dried, stored for 1 day to 2 weeks at 25° C. or 4° C., and rehydrated, developed into morulae/blastocysts in vitro and 25–34 (20%–29%) of these developed into normal offspring when transferred to foster mothers. Although a lesser percentage (76%) of fertilized eggs that had been injected with CZB-suspended freeze-dried sperm that had been stored for 1 month at 25° C. prior to rehydration, developed into morulae/blastocysts, 16 (18%) of these developed into normal offspring when transferred to foster mothers. Nine (28%) of 32 transferred embryos derived from fertilized eggs that had been injected with CZB-suspended sperm heads, freeze-dried and stored at 4° C. for 3 months, developed into normal offspring. In summary, when CZB-suspended freeze-dried sperm were employed, a total of 143 live offspring were produced after transfer of 562 embryos, developed from 664 oocytes that survived microsurgery and fertilized normally, an overall success rate of 21.5%.

The majority (79%–91%) of fertilized eggs, that had been injected with DMEM-suspended sperm heads, that had been freeze-dried, stored for 1 day to 1 month at 25° C. or up to 3 months at 4° C., also developed into morulae/blastocysts in vitro. In summary, a total of 92 live offspring were produced after transfer of 326 embryos, developed from 493 oocytes that survived microsurgery and fertilized normally, an overall success rate of 18.7%.

As illustrated in FIG. 1b, all of the offspring grew normally. Their sex ratio was about 1:1. Two fully grown females and two males from each of the 12 experimental groups were randomly selected and mated. All proved to be fertile and normal sized litters (8 to 12) were produced.

The Effect of Shipping Freeze-dried Sperm on Fertilization Competency

Of the spermatozoa that were shipped to and from Japan, and reconstituted upon their return to Honolulu, a randomly selected 29 spermatozoa were individually injected into oocytes. Twenty three oocytes (79%) survived and were fertilized normally. Nineteen (83%) developed into morulae/blastocysts in vitro. Three (16%) of those reached full term after transfer to a foster mother. All three (2 females and 1 male) grew into fertile adults.

In view of the foregoing Examples, it has been demonstrated that mouse spermatozoa can retain their genetic integrity after freeze-drying. There is no reason to believe that spermatozoa from other species, including invertebrates and vertebrates, would behave differently.

While the invention has been described herein with reference to the preferred embodiments, it is to be understood that it is not intended to limit the invention to the specific forms disclosed. On the contrary, it is intended to cover all modifications and alternative forms falling within the spirit and scope of the invention.

TABLE 1

Development of Mouse Oocytes Injected With Freeze-Dried Spermatozoa

| Sperm | Sample Storage | | Sperm-Injected Oocytes | | | | | |
|---|---|---|---|---|---|---|---|---|
| | | | Total No. Oocytes | No. (%) | No. (%) Oocytes | No. (%) Reaching Morulae/ | No. Embryos Transferred | No. (overall %) |
| Suspending Medium | Temp. (C.) | Time Period | Injected (Exp. No.) | Oocytes Survived | Fertilized Normally | Blastocyst Stage | (No. Foster Females) | [range]* of Live Offspring |
| CZB | 25° | 1 day | 155 (5) | 135 (87) | 133 (99)[a] | 120 (90)[e] | 116 (8) | 34 (29) [0–71] |
| | | 2 weeks | 158 (4) | 144 (91) | 141 (98)[a] | 131 (93)[f] | 126 (8) | 25 (20) [0–30][k] |
| | | 1 month | 130 (4) | 120 (92) | 117 (98)[a] | 89 (76)[g] | 87 (5) | 16 (18) [5–33][k] |
| | 4° | 2 weeks | 137 (4) | 126 (92) | 123 (98)[a] | 114 (93)[e] | 105 (7) | 27 (26) [0–45] |
| | | 1 month | 131 (4) | 117 (89) | 112 (96)[a] | 98 (88)[h] | 96 (6) | 32 (33) [14–65][l] |
| | | 3 months | 40 (2) | 38 (95) | 38 (100)[b] | 35 (92)[h] | 32 (2) | 9 (28) [26–31] |
| DMEM | 25° | 1 day | 128 (3) | 116 (91) | 104 (90)[b] | 95 (91)[e] | 95 (6) | 29 (31) [18–47][l] |
| | | 2 weeks | 109 (2) | 102 (94) | 85 (83)[c] | 67 (79)[i] | 60 (3) | 8 (13) [0–20][m] |
| | | 1 month | 113 (2) | 106 (94) | 74 (70)[d] | 47 (64)[j] | 47 (3) | 8 (17) [0–24] |
| | 4° | 2 weeks | 83 (2) | 79 (95) | 79 (100)[a] | 69 (87)[h] | 56 (3) | 20 (36) [21–46][l] |
| | | 1 month | 152 (3) | 137 (90) | 135 (99)[a] | 114 (84)[h] | 54 (3) | 22 (41) [15–60][m] |
| | | 3 months | 17 (1) | 16 (94) | 16 (100) | 14 (88) | 14 (1) | 5 (35) [35–35] |

*Range of % offspring per foster mother.
Statistical Significance:
[a] vs. [c, d]: $p < 0.005$
[b] vs. [d]: $p < 0.005$
[e] vs. [g, j]: $p < 0.005$
[f] vs. [g, i, j]: $p < 0.005$
[h] vs. [j]: $p < 0.005$
[n] vs. [k]: $p < 0.01$
[n] vs. [m]: $p < 0.01$
[l] vs. [m]: $p < 0.01$

We claim:

1. A membrane-damaged freeze-dried spermatozoon or freeze-dried spermatozoon head, having a moisture content of less than 1% and comprising a nucleus that has retained genetic integrity, wherein after rehydration and insertion of the nucleus into an isolated oocyte, the nucleus fertilizes the oocyte, and the retained genetic integrity of the nucleus is sufficient to result in the development of an embryo and the production of a live offspring.

2. The freeze-dried spermatozoon or spermatozoon head of claim 1, wherein the spermatozoon is demembranated prior to becoming freeze-dried.

3. The freeze-dried spermatozoon or spermatozoon head of claim 1, wherein the spermatozoon or spermatozoon head is from an invertebrate.

4. The freeze-dried spermatozoon or spermatozoon head of claim 3, wherein the invertebrate is a sea urchin, a lobster, an abalone, or a shellfish.

5. The freeze-dried spermatozoon or spermatozoon head of claim 1, wherein the spermatozoon or spermatozoon head is from a vertebrate.

6. The freeze-dried spermatozoon or spermatozoon head of claim 5, wherein the vertebrate is a fish, an amphibian, a reptile, a bird, or a mammal.

7. The freeze-dried spermatozoon or spermatozoon head of claim 5, wherein the vertebrate is a human.

8. The freeze-dried spermatozoon or spermatozoon head of claim 5, wherein the vertebrate is a mouse.

9. A method for freeze-drying spermatozoa or isolated spermatozoa heads to obtain a freeze-dried spermatozoon nucleus that retains genetic integrity sufficient to produce a live offspring, after rehydration and insertion of the nucleus into an isolated oocyte, comprising the steps of:

collecting live spermatozoa;

optionally isolating spermatozoa heads from the spermatozoa;

suspending the spermatozoa or spermatozoa heads in a physiological suspension medium;

freezing the suspension of spermatozoa or spermatozoa heads to form frozen spermatozoa or frozen spermatozoa heads;

drying the frozen spermatozoa or frozen spermatozoa heads to a moisture level of less than 1% to form freeze-dried spermatozoa having damaged membranes or freeze-dried spermatozoa heads, wherein at least one membrane-damaged freeze-dried spermatozoon or freeze-dried spermatozoon head comprises a nucleus that has retained genetic integrity, wherein after rehydration and insertion of the nucleus into an isolated oocyte, the nucleus fertilizes the oocyte, resulting in the development of an embryo and the production of a live offspring.

10. The method of claim 9, wherein the optional step of isolating the sperinatozoa heads from the spermatozoa includes demembranating the spermatozoa.

11. The method of claim 10, wherein the demembranating step comprises treatment of the spermatozoa with a detergent and, optionally, a surfactant.

12. The method of claim 9, wherein the moisture level is less than 0.01%.

13. The method of claim 9, wherein the moisture level is less than 0.001%.

14. The method of claim 9, wherein the moisture level is less than 0.00001%.

15. The method of claim 9, wherein the spermatozoa or spermatozoa heads are from a vertebrate.

16. The method of claim 15, wherein the vertebrate is a fish, an amphibian, a reptile, a bird, or a mammal.

17. The method of claim 15, wherein the vertebrate is a human.

18. The method of claim 15, wherein the vertebrate is a mouse.

19. The method of claim 9, wherein the spermatozoa or spermatozoa heads are from an invertebrate.

20. The method of claim 19, wherein the invertebrate is a sea urchin, a lobster, an abalone, or a shellfish.

21. The method of claim 9, wherein the freezing step is carried out at −196° C. for about 10 minutes.

22. The method of claim 9, further comprising the step of storing the freeze-dried spermatozoa or spermatozoa heads for a period of time after the drying step.

23. The method of claim 22, wherein storage is at ambient temperature.

24. The method of claim 22, wherein storage is at about 4° C.

25. The method of claim 22, wherein storage is at −20° C. or below.

26. The method of claim 22, wherein the storage time period is up to three months.

27. The method of claim 22, wherein the storage time period is up to about one year.

28. The method of claim 22, wherein the storage time period is greater than one year.

29. An ampule containing the freeze-dried spermatozoa or spermatozoa heads produced in the drying step of the method of claim 9.

* * * * *